(12) United States Patent
Olsson

(10) Patent No.: US 9,625,602 B2
(45) Date of Patent: Apr. 18, 2017

(54) SMART PERSONAL COMMUNICATION DEVICES AS USER INTERFACES

(75) Inventor: Mark S. Olsson, La Jolla, CA (US)

(73) Assignee: SEESCAN, INC., San Diego, CA (US)

( * ) Notice: Subject to any disclaimer, the term of this patent is extended or adjusted under 35 U.S.C. 154(b) by 1355 days.

(21) Appl. No.: 12/939,591

(22) Filed: Nov. 4, 2010

(65) Prior Publication Data

US 2011/0109437 A1 May 12, 2011

Related U.S. Application Data

(60) Provisional application No. 61/259,519, filed on Nov. 9, 2009.

(51) Int. Cl.
*G08B 5/22* (2006.01)
*G01V 3/15* (2006.01)
*G01N 21/954* (2006.01)
*H04M 1/725* (2006.01)

(52) U.S. Cl.
CPC ............. *G01V 3/15* (2013.01); *G01N 21/954* (2013.01); *H04M 1/7253* (2013.01); *H04M 1/72527* (2013.01); *H04M 2250/10* (2013.01)

(58) Field of Classification Search
CPC ... G01V 3/15; G01N 21/954; H04M 1/72527; H04M 1/7253; H04M 2250/10
USPC ....................................... 340/8, 8.1; 702/130
See application file for complete search history.

(56) References Cited

U.S. PATENT DOCUMENTS

2003/0164789 A1* 9/2003 Taylor et al. ................... 342/22
2006/0282280 A1* 12/2006 Stotz et al. ....................... 705/1
2011/0191058 A1* 8/2011 Nielsen et al. ............... 702/130

* cited by examiner

*Primary Examiner* — Edwin Holloway, III
(74) *Attorney, Agent, or Firm* — Steven C. Tietsworth, Esq.

(57) ABSTRACT

A personal communication device or "smart phone" is connected to a utility locator system or pipe inspection system and serves as a user interface, communication interface, and control system for such systems.

18 Claims, 6 Drawing Sheets

SMART PERSONAL COMMUNICATION DEVICES AS USER INTERFACES

CROSS-REFERENCE TO RELATED APPLICATION

This application claims priority based on the identically entitled U.S. Provisional Application Ser. No. 61/259,519 filed by Mark S. Olsson et al. on Nov. 9, 2009 and assigned to SeekTech, Inc.

FIELD OF THE INVENTION

This invention relates generally to electronic personal communication devices and in particular to their adaptation as user-interface nodes in underground utility locating and pipe inspection systems.

DESCRIPTION OF THE RELATED ART

The evolution of smart machines over the last fifty years has exhibited major advances in miniaturization, connectivity and display systems. With regards in particular to display systems, a wide array of useful devices exists which have particular designs and varying functional requirements for display. Small video cameras have one class of displays, while pipe-inspection systems have another. Computing platforms for calculating calories and weight loss in exercise programs have information display requirements when they are built into small devices meant to be carried or worn. Diving computers have their own kinds of display, as well. Other useful devices impose different requirements on the means of displaying information, such as underground utility locators which display detection information, bore scopes which display visual images, camera control devices which relay camera images and provide user controls for remote camera, and the like. In most of these devices a combination of computational power and display comes together for some specific purpose.

SUMMARY OF THE INVENTION

In accordance with the present invention a personal communication device or "smart phone" is connected to a utility locator system or pipe inspection system and serves as a user interface, communication interface, and control system for such systems.

DETAILED DESCRIPTION

With the advent of highly miniaturized computing devices for personal communication, such as the Motorola "Droid" and the Apple "iPhone" and "iPad" as examples, with improving resolution and computational power, the potential exists for adapting these and similar hand-held devices to serve as front-end interface devices for a wide array of applications such as underground utility locating and pipe inspection systems.

The present invention provides hardware and software based adaptive connection for such devices to serve as control or display units for utility locating and pipe inspection systems utilizing connectivity such as by USB or wireless means built into such communication devices.

The modern personal communication device is noted for its enhanced and versatile display capabilities. For example, the current version of the Motorola/Verizon Droid personal communication device includes a 3.7 inch display screen with a 480×854 pixel resolution. It supports HTML5 and DVD-quality video replay. The Apple iPhone personal communication device, its predecessor in this product space, has a 3.5 inch display screen with 480×320 pixel resolution, and finger-tip scrolling. These two devices, which are also known as "smart phones" are, examples of the class of device referred to in this disclosure as personal communication devices. The personal communication pad, such as the Apple iPad device or Hewlett-Packard Slate device, is also included in the family of personal communication devices referred to herein. These types of personal communication devices are expected to improve rapidly as the market expands.

Figure 1A:
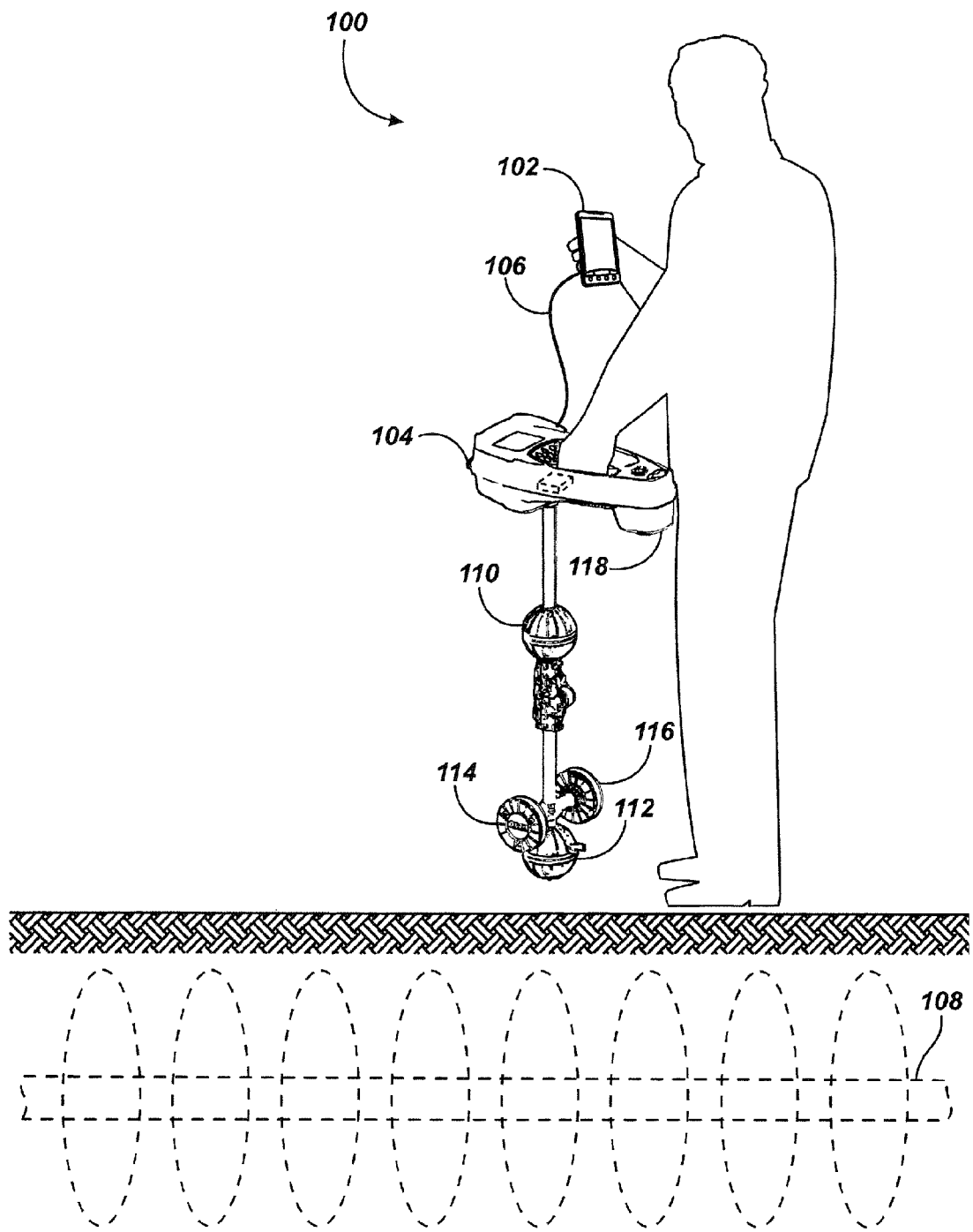
FIG. 1A is a diagrammatic illustration of an exemplary embodiment of the present invention in the form of underground utility detection and location device.

Referring to FIG. 1A, an underground utility locating system 100 is illustrated that is adapted to communicate with a hand-held display and image capture personal communication device 102. In FIG. 1A the personal communication device 102 is connected to a man portable omnidirectional utility locator 104 by a USB cable connector 106 and serves as a display device for the locator 104. FIG. 1A illustrates the locator detecting electromagnetic signals from an underground pipe 108. The locator 104 detects variations in fields by means of a pair of omnidirectional antennas 110, 112 and a pair of gradient antennas 114, 116. The locator 104 is independently powered by a set of on-board batteries 118 which may provide supplementary power as well to the hand-held device 102 as well as optionally recharging the batteries in the hand-held device 102. A mounting bracket on an attached holster (not illustrated) may also be provided to support personal communication device 102. Display on the personal communication device 102 is governed by custom application software on the personal communication device 102. Initial A-to-D conversion of antenna signals and computation of field vectors may be done within the locator 104 or within the personal communication device 102. Software on the locator 104 and on the hand-held device 102 controls exchange of data and command updates across the USB cable 106. The locator 104 can transmit to the personal communication device 102 a paint-event time stamp or time tag which indicates the time that the location of a buried utility was determined. In an alternate embodiment, a wireless connection such as Bluetooth or the like is used between locator 104 and personal communication device 102. By way of example, the locator 104 may be of the various types disclosed in U.S. Pat. Nos. 7,009,399; 7,136,765; 7,332,901; 7,336,078; 7,443,154; 7,498,797; 7,498,816; 7,518,374; 7,619,516; 7,733,077; 7,741,848; 7,755,360; and 7,830,149, all assigned to SeekTech, Inc., the entire disclosures of all of which are hereby incorporated by reference. The locator 104 may also be of the type disclosed in published U.S. Patent Application Pub. No. US 2010/0272885 A1 published on Oct. 28, 2010 and based on U.S. patent application Ser. No.

12/827,993 filed by Mark S. Olsson et al. on Jun. 30, 2010 and entitled "Marking Paint Applicator for Portable Locator", also assigned to SeekTech, Inc., the entire disclosure of which is hereby incorporated by reference.

Figure 1B:
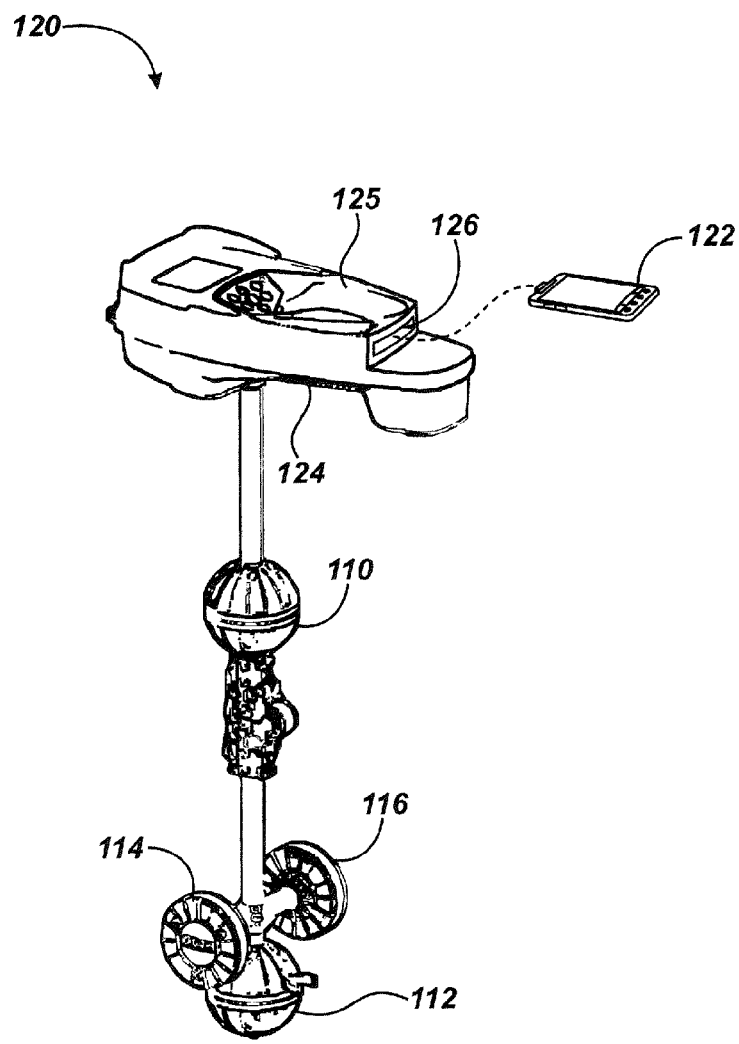
FIG. 1B is an alternate embodiment of the present invention for the same application.
Figure 1B:
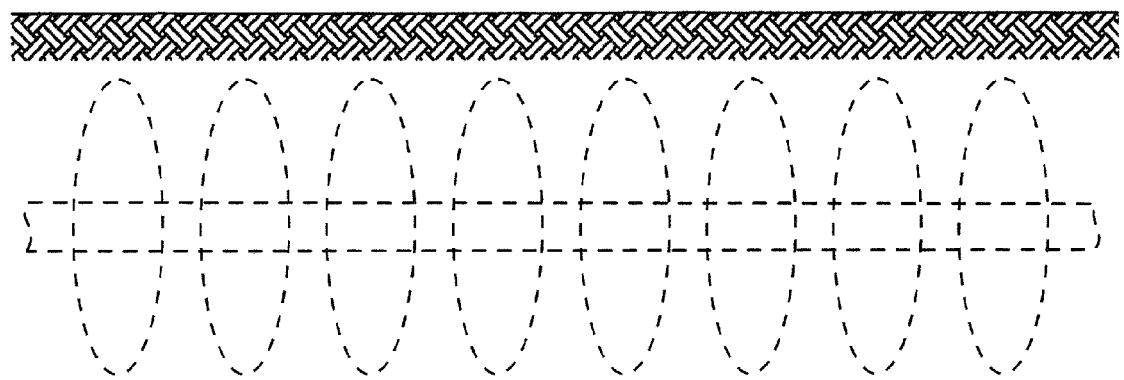

Referring to FIG. 1B, an alternate embodiment of an underground utility locating system 120 combines a hand-held personal communication device 122 with a utility locator 124. In FIG. 1B, the personal communication device 122 seats into a formed receptacle 125 in the outer shell of the locator 124. Within the receptacle a USB connection plug 126 plugs into the USB connector on the personal communication device 122.

Hand-held devices of the kind referred to herein typically have on-board location-determining software which uses on-board GPS sensors, or cell-tower triangulation, or other means to resolve and display the unit's present location in conjunction with a map. The specialized adapted device shown in these figures may include, for example, an algorithm for plotting such locations determined during a locate activity as an overlay on a local map. Data thus generated may be stored on the hand-held device or transmitted to a database on a remote server using the cellular or wireless capabilities built into the hand-held device. Such information may likewise be transferred from the hand-held device to a USB storage device (e.g. thumb drive) at the convenience of the operator, for transfer to other computers or inclusion in reports or databases, for example.

Figure 2:
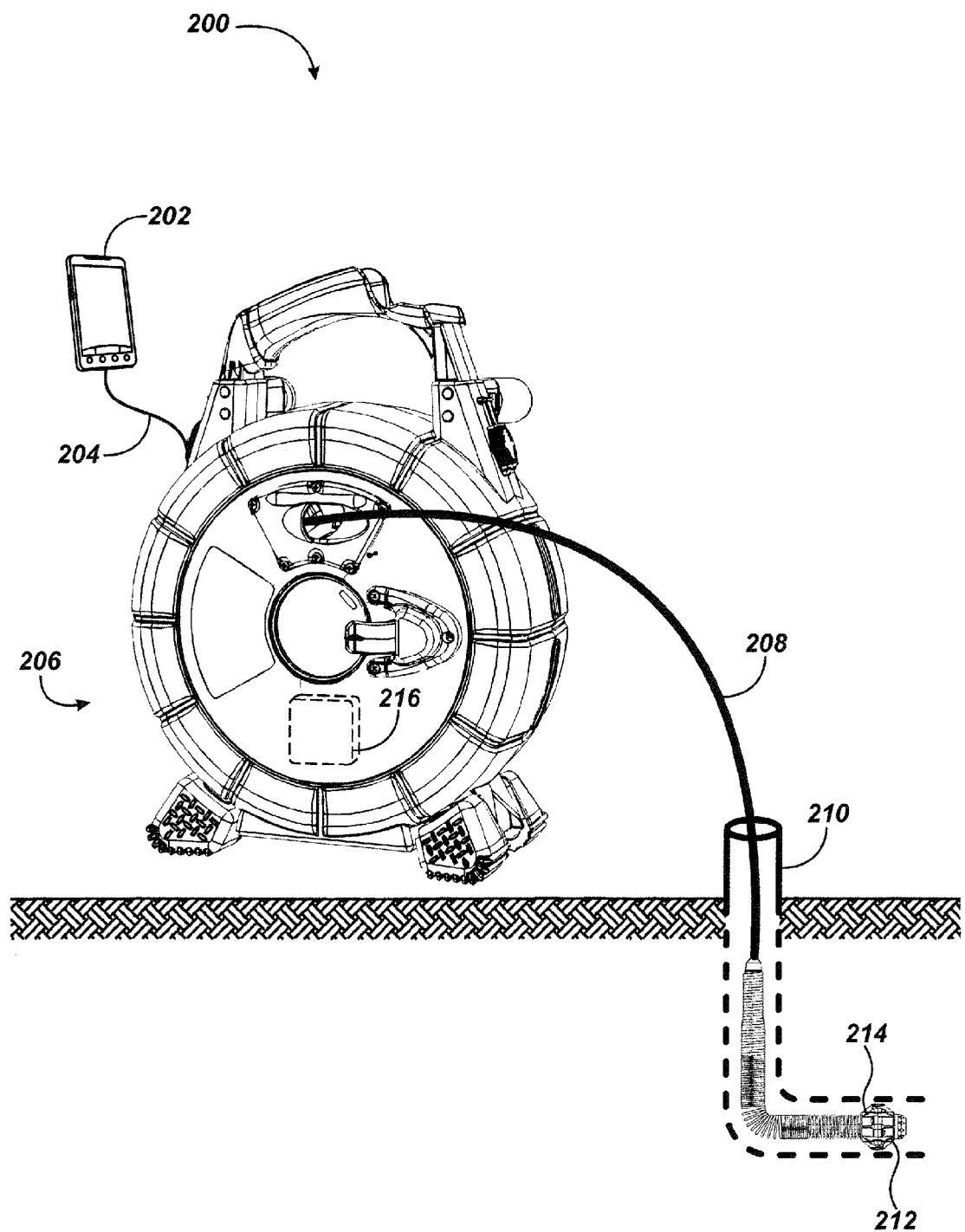
FIG. 2 is an illustration of an alternate embodiment of the present invention in the form of a pipe inspection system.

Referring to FIG. 2, a pipe inspection system 200 includes a hand-held personal communication device 202 that is connected by a USB cable 204 to a lightweight portable pipe inspection cable and reel assembly 206. The personal communication device 202 and the cable and reel assembly 206 can alternatively be connected via Blue Tooth or other wireless link. A push-cable 208 of the pipe inspection system 200 is illustrated entering a pipe 210 for the purpose of inspecting the interior of the pipe. A camera head 212 is operatively connected to the distal end of the push-cable 208. The push-cable 208 has at least one composite push rod and a plurality of shielded cables, giving it a resilient flexible construction that enables it to be pushed down turns in the pipe 210 while at the same time transmitting power and data between above-ground circuitry and the camera head 212. Visual images of the pipe interior may be captured by the software loaded into the hand-held personal communication device 202, and sent as attachments by electronic mail or transferred to a USB thumb drive by the user. Custom software onboard the personal communication device 202 can assist the operator in managing images, controlling the camera head 212 of the pipe inspection system 200, and create and manage reports for business purposes concerning findings of the inspection. The hand-held personal communication device 202 typically includes imaging devices, on-board GPS, compass and tilt sensors and mapping software which can be incorporated into such reports. Geo-tagged images with compass and tilt data may also be included in such reports. Within the c camera head 212 a built-in transmitting sonde 214 is similarly controlled by the hand-held personal communication device 202 custom software using interface electronics 216 built into the cable and reel assembly 206 in this embodiment. The cable and reel assembly 206 may be of the type disclosed in pending U.S. patent application Ser. No. 12/704,808 entitled "Pipe Inspection System with Replaceable Cable Storage Drum" filed by Mark S. Olsson et al. on Feb. 12, 2010 and published on Aug. 19, 2010 as US 2010/0208056-A1, also assigned to SeekTech, Inc., the entire disclosure of which is hereby incorporated by reference. See also U.S. Pat. Nos. 6,545,704 and 6,958,767 and pending U.S. patent application Ser. No. 12/766,742 entitled "Pipe Inspection Cable Counter and Overlay Management System" filed by Mark S. Olsson et al. on Apr. 23, 2010, all assigned to SeekTech, Inc., the entire disclosures of all which are hereby incorporated by reference.

Figure 3:
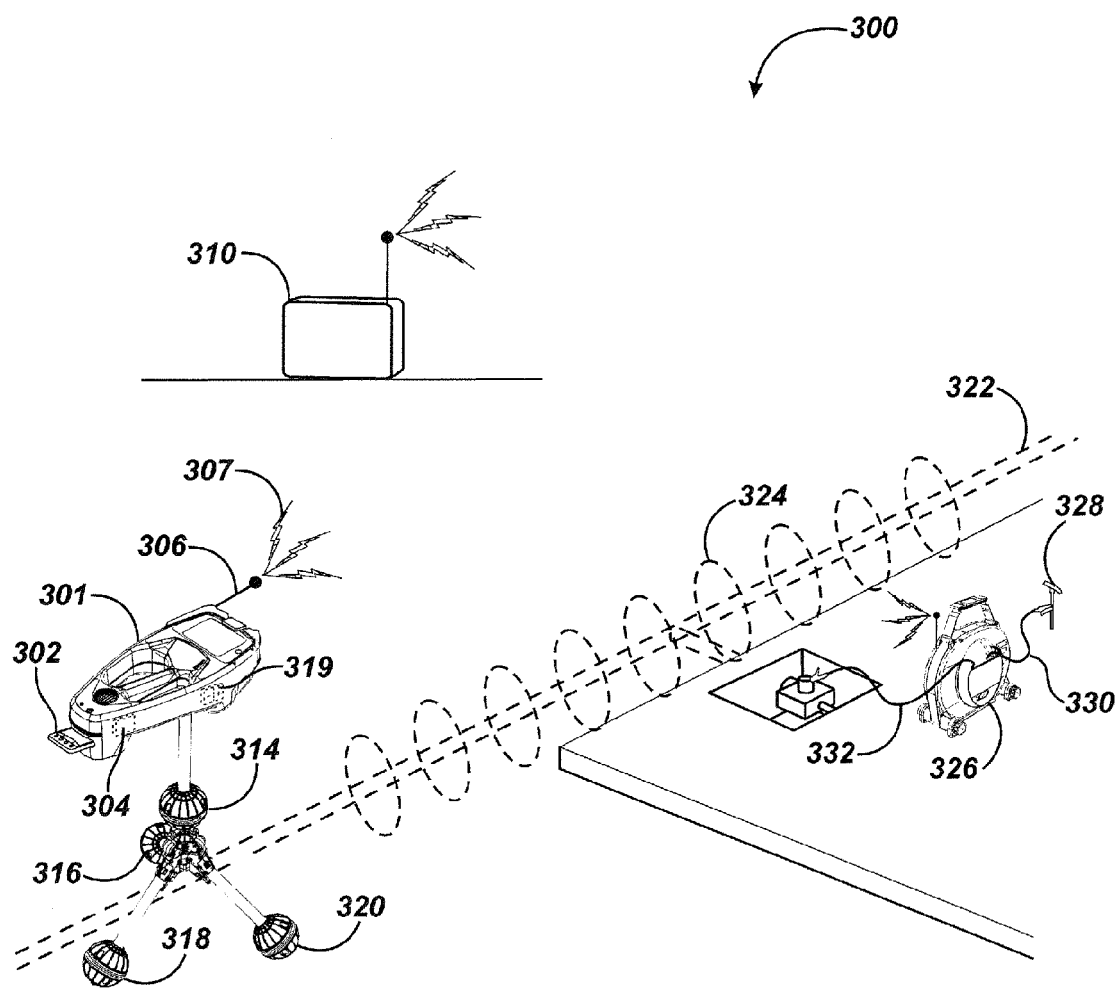
FIG. 3 illustrates an alternate embodiment of the present invention adapted for job-site mapping and management.

Referring to FIG. 3, an alternate embodiment of the present invention has a smart phone or hand-held personal communication device 302 is integrated into a locating and mapping system 300, used on construction or development job sites, for example. In FIG. 3, the hand-held personal communication device 302 is removably seated in a cradle on a three-legged (tripod) locator 301 in such a way that a USB connector plug (not visible) or other interface connects the hand-held personal communication device 302 to locator 301. A compact coil cord (not illustrated) may be used to allow the connected hand-held personal communication device 302 to be used apart from, but still connected to, the locator 301, or wireless means may be used for this purpose.

The locator 301 (FIG. 3) uses four omnidirectional antenna arrays, 314, 316, 318, and 320 to detect an electromagnetic field 324 being generated along a buried pipe 322 by a connected transmitter 326. The transmitter 326 may be of the type disclosed in pending U.S. patent application Ser. No. 11/961,858 filed by Ray Merewether et al. on Dec. 20, 2007 and entitled "High-Q Self-Tuning Locating Transmitter", also assigned to SeekTech, Inc., the entire disclosure of which is hereby incorporated by reference. Alternatively, the transmitter 326 may include self-tuning resonator circuitry of the type disclosed in U.S. Pat. No. 7,276,910 also assigned to SeekTech, Inc., the entire disclosure of which is hereby incorporated by reference. The transmitter 326 is connected to the pipe 322 with a lead 332 and to a grounding stake 328 with another lead 330. The transmitter 326 may be equipped with wireless transmit and receive capabilities and optionally may be combined with a separate positional beacon 310 for assisting in positional triangulation, and/or with a GPS or DGPS capability. The beacon 310 is equipped with wireless capabilities and optionally also has GPS capabilities. When deployed in a fixed surveyed location, for example, a beacon such as 310 can be used as a DGPS or RTK unit to rectify fine errors in GPS computation.

Locator 301 may provide supplementary power to the hand-held personal communication device 302 from its on-board batteries 304 as needed and serve to recharge the internal batteries of personal communication device 302. The wireless connection 306 built into personal communication device 302 enables the personal communication device 302 to exchange location information 307 with transmitter 326 or with one or more remote beacons such as 310. By use of this connection to one or more beacons such as 310 as well as its built-in GPS capability, hand-held personal communication device 302 as customized in this application may integrate precise GPS-based location information into a map of the job site. As in other embodiments, information generated by a specific application in the hand-held personal communication device 302 may be transferred across a network by wireless means, or transferred to a portable storage device across the USB connection for integration into a database, reports or other information structures. A true-north compass 319 may be integrated into the system enabling a composite visual representation of the site to be collected by simply taking images with the built-in camera in the hand-held personal communication device 302 and integrating them with location and orientation metadata.

The systems described herein use a hand-held communication device (such as a smart phone) as a display and computation interface. With similar adaptors suited to the individual application, the same hand-held device can be connected, for example, to a wall-scanner for stud locating, a bicycle trip mapping computing device, a video boroscope used in the inspection of wall interiors or other constrained voids, a dive computer utilizing a waterproof casing combined with appropriate sensors, a portable video camera, or other application.

Figure 4:
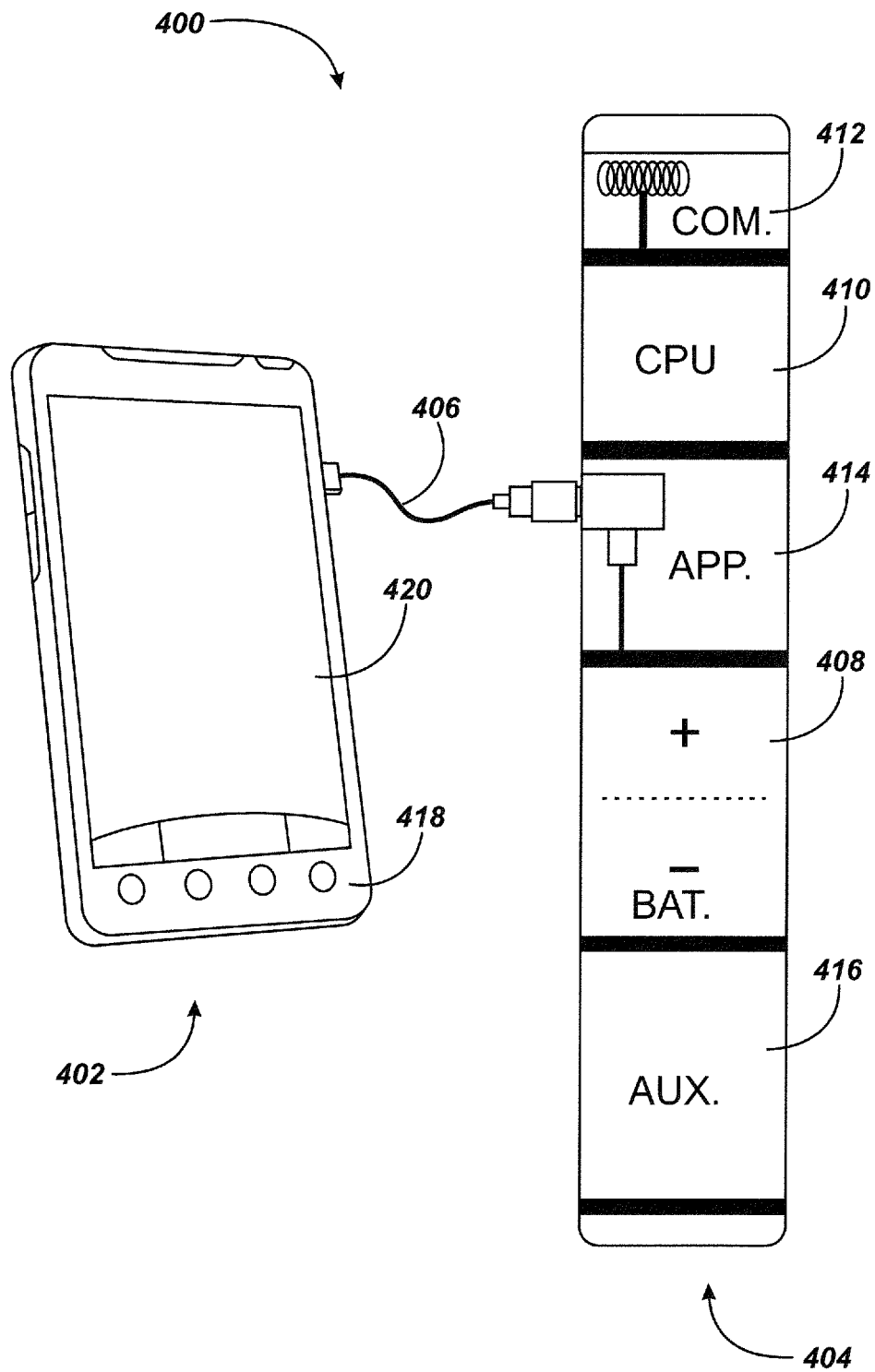
FIG. 4 is a diagrammatic illustration of the physical components of an embodiment of the present invention.

Referring to FIG. 4, a functional block diagram 400 illustrates the hardware components of the disclosed embodiments in general form. A smart phone, or hand-held personal communication device 402 is connected by means of an integrated USB connection 406 to a specialized hardware adaptor block 404. The hardware adaptor block 404 typically includes a battery section 408 for supplementary power for both the specific application and the hand-held personal communication device 402. The USB connection 406 may carry both data and power. Within the external hardware adaptor block 404, a central processor 410 may be used. Depending on the application, an external communication block 412 for data transfer by wireless means or the like may be required within the hardware adapter block 404, supplementary to the communication capabilities of the hand-held personal communication device 402. Circuitry 414 supporting the specific application is embedded in the hardware block 404. Auxiliary components 416 may be required such as specialized sensors or other application-specific components.

Controls 418, display 420 (FIG. 4) and communication capabilities as well as data storage are typically found onboard the personal communication device 402. These capabilities may alternatively be incorporated into the adaptor block 404 according to the particular implementation needs. Where the adaptor block 404 includes a separate central processor 410, software may control processing load sharing between the adaptor's central processor 410 and the processing capability of the personal communication device 402.

Figure 5:
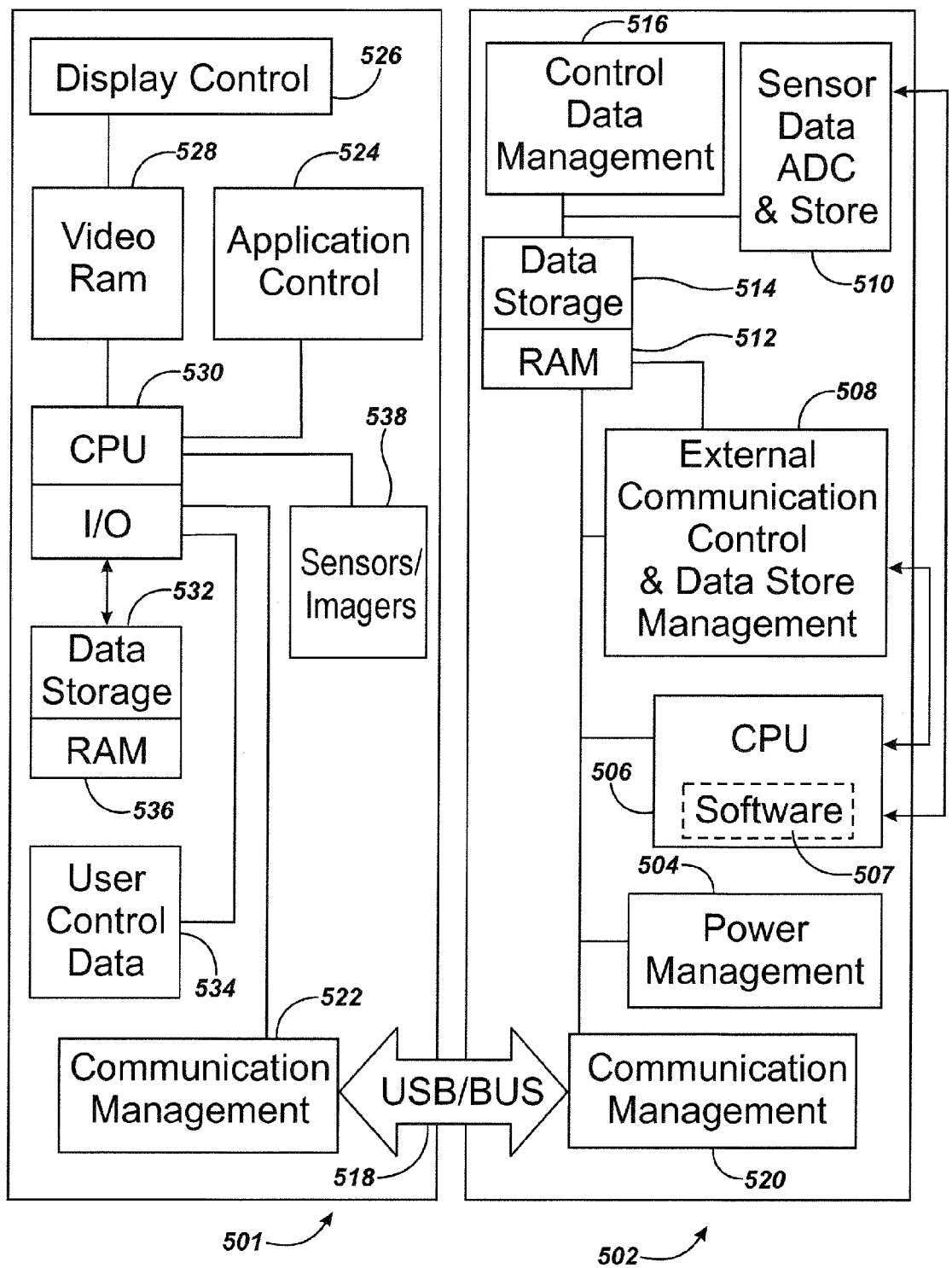
FIG. 5 is a functional diagram illustrating the software components of an embodiment of the present invention.

Referring to FIG. 5 a block diagram of software functionality 500 illustrates the relationship between software architecture of the hand-held device 501 and application software architecture 502 of the adaptive extension being used. The specific application will govern the detailed components of the software. Within the application software architecture 502, a power-management software block 504 controls power sensing and supply and sharing if applicable. For some applications a separate central processing unit 506 is required for preliminary processing. Software 507 loads into and runs on CPU 506. Where applicable a communications software module 508 governs external signal exchanges for the application block. On-board sensor data conversion and storage is controlled by a separate sensor software block 510. A control data management module 516 manages control signals from the user interface in the hand-held device 501. A RAM storage block 512 and permanent data storage block 514 manage memory and writing to storage. Communication management software block 520 governs timing and exchange of data with hand-held device 501 across the USB bus 518.

Referring still to FIG. 5, within the hand-held device 501 a similar communication control module 522 controls communication with application software 502. The hand-held device 501 contains software blocks for managing specific application data 524, display control 526, video RAM 528, data storage 532 and RAM data transfer 536. A central processing unit 530 coordinates data streams, file management, and I/O. User control data 534 is stored in memory in its own block. As with the application block 503 the detailed architecture of application software 524 will depend on the particular use to which the embodiment is being put.

Clearly, other embodiments and modifications of this invention may occur readily to those skilled in the art in view of these teachings. Therefore, the protection afforded the present invention is to be limited only by the following claims, which include all such embodiments and modifications when viewed in conjunction with the above specification and accompanying drawings.

I claim:

1. An underground utility locating system, comprising:
a portable locator including a plurality of omnidirectional antennas for detecting emissions from a buried utility;
a personal communication device operatively connected to the portable locator for receiving information from the portable locator representing a location of the buried utility; and
programming in the personal communication device for storing and transmitting the location of the buried utility;
wherein the portable locator has a receptacle for removably receiving the personal communication device and a first connector for mating with a second connector of the portable communication device.

2. The locating system of claim 1 wherein the programming in the personal communication device can overlay the location of the buried utility on a local map displayed by the personal communication device.

3. The locating system of claim 1 wherein the portable locator has a battery power supply and circuitry for delivering power to the personal communication device.

4. The locating system of claim 1 wherein the personal communication device has GPS circuitry that enables the local map to be generated.

5. The locating system of claim 1 wherein the personal communication device includes programming for generating and transmitting reports indicating the location of the buried utility.

6. The locating system of claim 1 wherein the portable locator and the personal communication device are operatively connected with a USB cable.

7. The locating system of claim 1 wherein the portable locator and the personal communication device are operatively connected with a wireless communications link.

8. The locating system of claim 1 wherein the portable locator has programming for generating a time tag of the location of the buried utility and transmitting the time tag to the personal communication device.

9. The locating system of claim 1 wherein the portable locator has a paint marking applicator.

10. An underground utility locating system, comprising:
a portable locator that detects electromagnetic emissions from a buried utility;
a personal communication device operatively connected to the portable locator for receiving information from the portable locator representing a location of the buried utility;
programming in the personal communication device for storing and transmitting the location of the buried utility;
a cable storage drum;
a resilient flexible push-cable stored in coiled fashion inside the drum;
a rotatable support that carries the drum so that the push cable can be paid out from the drum and re-wound back into the drum;

a camera head operatively coupled to a distal end of the push-cable for capturing images of the inside of a pipe as the push-cable is paid out from the cable storage drum to force the camera head down an interior of the pipe;

a personal communication device operatively connected to the camera head for receiving images from the camera head; and programming in the personal communication device for managing the images;

wherein the portable locator has a receptacle for removably receiving the personal communication device and a first connector for mating with a second connector of the portable communication device.

11. The locating system of claim 10 wherein the programming allows the camera head to be controlled through the personal communication device.

12. The locating system of claim 10 wherein the programming allows the personal communication device to generate, store and transmit pipe inspection reports.

13. The locating system of claim 10 wherein the programming allows the personal communication device to control a sonde inside the camera head.

14. An underground utility locating system, comprising:
a portable locator that detects electromagnetic emissions from a buried utility;

a personal communication device operatively connected to the portable locator for receiving information from the portable locator representing a location of the buried utility; and programming in the personal communication device for storing and transmitting the location of the buried utility;

wherein the portable locator has a receptacle for removably receiving the personal communication device and a first connector for mating with a second connector of the portable communication device; and wherein the programming allows the personal communication device to generate geo-tagged images.

15. An underground utility locating system, comprising:
a portable locator that detects electromagnetic emissions from a buried utility;

a personal communication device operatively connected to the portable locator for receiving information from the portable locator representing a location of the buried utility; and programming in the personal communication device for storing and transmitting the location of the buried utility;

wherein the portable locator has a receptacle for removably receiving the personal communication device and a first connector for mating with a second connector of the portable communication device; and wherein the programming in the personal communication device includes programming for computation of electromagnetic field vectors of signals received from one or more antennas of the portable locator.

16. An underground utility locating system, comprising:
a portable tripod locator that detects electromagnetic emissions from a buried utility;

a personal communication device operatively connected to the portable locator for receiving information from the portable locator representing a location of the buried utility; and programming in the personal communication device for storing and transmitting the location of the buried utility;

wherein the portable locator has a receptacle for removably receiving the personal communication device and a first connector for mating with a second connector of the portable communication device.

17. An underground utility locating system, comprising:
a portable locator including a plurality of omnidirectional antennas for detecting electromagnetic emissions from a buried utility;

a personal communication device operatively connected to the portable locator for receiving information from the portable locator representing a location of the buried utility; and programming in the personal communication device for storing and transmitting the location of the buried utility; and a transmitter for generating a current to be applied to the buried utility to generate the electromagnetic emissions;

wherein the portable locator has a receptacle for removably receiving the personal communication device and a first connector for mating with a second connector of the portable communication device.

18. The locating system of claim 10 wherein the rotatable support is mounted inside a clam shell housing that encloses the cable storage drum.

* * * * *